(12) United States Patent
Corson et al.

(10) Patent No.: US 7,247,494 B2
(45) Date of Patent: Jul. 24, 2007

(54) SCANNER WITH ARRAY ANTI-DEGRADATION FEATURES

(75) Inventors: John F. Corson, Mountain View, CA (US); Russell A. Parker, San Jose, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 371 days.

(21) Appl. No.: 10/788,547

(22) Filed: Feb. 27, 2004

(65) Prior Publication Data

US 2005/0191756 A1  Sep. 1, 2005

(51) Int. Cl.
*G01N 21/00* (2006.01)
*G01N 27/416* (2006.01)
*C12Q 1/68* (2006.01)
*B32B 5/02* (2006.01)
*G01N 7/00* (2006.01)

(52) U.S. Cl. .................. 436/164; 422/82.05; 436/151; 436/140; 356/73; 356/311; 356/427; 435/6; 73/23.2

(58) Field of Classification Search ............ 422/82.05; 436/164; 356/73, 311, 427, 344
See application file for complete search history.

(56) References Cited

U.S. PATENT DOCUMENTS

| | | | | |
|---|---|---|---|---|
| 4,968,148 A * | 11/1990 | Chow et al. | ................. | 356/427 |
| 5,459,325 A * | 10/1995 | Hueton et al. | ............ | 250/458.1 |
| 5,646,411 A * | 7/1997 | Kain et al. | ................ | 250/458.1 |
| 5,721,435 A * | 2/1998 | Troll | ...................... | 250/559.29 |
| 5,784,152 A * | 7/1998 | Heffelfinger et al. | ......... | 356/73 |
| 5,959,191 A * | 9/1999 | Lewis et al. | ............... | 73/31.05 |
| 6,043,880 A * | 3/2000 | Andrews et al. | ............ | 356/311 |
| 6,085,576 A * | 7/2000 | Sunshine et al. | .......... | 73/29.01 |
| 6,171,793 B1 * | 1/2001 | Phillips et al. | ................. | 435/6 |
| 6,266,995 B1 * | 7/2001 | Scott | ......................... | 73/23.2 |
| 6,329,661 B1 * | 12/2001 | Perov et al. | ............. | 250/461.2 |
| 6,355,934 B1 * | 3/2002 | Osgood et al. | .......... | 250/458.1 |
| 6,537,801 B1 * | 3/2003 | Ida et al. | ................. | 435/287.2 |
| 6,620,623 B1 * | 9/2003 | Yershov et al. | ............. | 436/172 |
| 6,841,391 B2 * | 1/2005 | Lewis et al. | ................ | 436/149 |
| 7,118,916 B2 * | 10/2006 | Matzinger | ..................... | 436/34 |
| 2001/0041366 A1 * | 11/2001 | Lewis et al. | ................ | 436/151 |
| 2003/0031596 A1 * | 2/2003 | Tanaami | .................. | 422/82.08 |

OTHER PUBLICATIONS

Condie Carmack- Agilent Technologies, TRC/Ozone Seminar Oct. 13, 2003 "Health Risks of Ozone" pp. 1-36.
Fare et al. "Effects of Atmospheric Ozone on MicroArray Data Quality" Anal Chem. 2003, 75, 4672-4675.

* cited by examiner

*Primary Examiner*—Jill Warden
*Assistant Examiner*—Neil Turk

(57) ABSTRACT

A reader is provided that, itself, addresses the issue of damage or degradation to arrays within the reader by virtue of air exposure. In doing so, experimental variability is reduced, and read/scan signal strength degradation is minimized for arrays/slides scanned or otherwise read toward the end of a run. The subject scanners employ a filter that reduces the amount of chemicals in the air inside the device that are harmful to the array, or the dye on the array. The implementation of adding a chemical filter to the reader device may be such that air is either drawn into or, alternatively, pushed through the filter into the same. It is possible that the entirety of the device may be provided with filtered air, or just the region holding slides to be scanned. Array readers so-constructed as well as associated methodology involving filtering incoming air while reading arrays are covered.

15 Claims, 2 Drawing Sheets

SCANNER WITH ARRAY ANTI-DEGRADATION FEATURES

FIELD OF THE INVENTION

This invention relates to arrays, such as polynucleotide or other biopolymer arrays (for example, peptide arrays).

BACKGROUND OF THE INVENTION

Array assays between surface bound binding agents or probes and target molecules in solution may be used to detect the presence of particular analytes or biopolymers in the solution. The surface-bound probes may be oligonucleotides, peptides, polypeptides, proteins, antibodies or other molecules capable of binding with target biomolecules in the solution. Such binding interactions are the basis for many of the methods and devices used in a variety of different fields, e.g., genomics (in sequencing by hybridization, SNP detection, differential gene expression analysis, identification of novel genes, gene mapping, finger printing, etc.) and proteomics.

One typical array assay method involves biopolymeric probes immobilized in an array on a substrate such as a glass substrate or the like. A solution containing target molecules ("targets") that bind with the attached probes is placed in contact with the bound probes under conditions sufficient to promote binding of targets in the solution to the complementary probes on the substrate to produce a binding complex that is bound to the surface of the substrate. The pattern of binding by target molecules to probe features or spots on the substrate produces a pattern, i.e., a binding complex pattern, on the surface of the substrate that is detected. This detection of binding complexes provides desired information about the target biomolecules in the solution.

The binding complexes may be detected by reading or scanning the array with, for example, optical means—although other methods may also be used, as appropriate for the particular assay. For example, laser light may be used to excite fluorescent labels attached to the targets, generating a signal only in those spots on the array that have a labeled target molecule bound to a probe molecule. This pattern may then be digitally scanned for computer analysis. Such patterns can be used to generate data for biological assays such as the identification of drug targets, single-nucleotide polymorphism mapping, monitoring samples from patients to track their response to treatment, assessing the efficacy of new treatments, etc.

In array fabrication, the quantities of biopolymer available, whether by deposition of previously obtained biopolymers or by in situ synthesis, are usually very small and expensive. Additionally, sample quantities available for testing are usually also very small and it is therefore desirable to simultaneously test the same sample against a large number of different probes on an array. These conditions require use of arrays with large numbers of very small, closely spaced features.

Scanning all these features can take considerable time. Over this time, it has been observed that an array may suffer degradation in the signal strength obtained toward the latter stages of a scan run. Further degradation may result if the arrayreading instrument holds multiple arrays, and takes even more time to completely scan all of the features on all of the arrays. The inventor(s) hereof recognized that microarray sensitivity to ozone is often causative of this observed effect.

Ozone has been found to attack and degrade the fluorescent dyes used in arrays—particularly Cyanine dyes, especially Cy5. Significant research has been undertaken in understanding, measuring and documenting this effect. See, e.g., Effects of Atmospheric Ozone on Microarray Data Quality by Fare, et al., Anal. Chem. 2003, Vol. 75 No. 17, 4672-4675. Indeed, it has been found that in just 5 minutes within a scanner, potential signal loss as a result of Cy5-ozone interaction can approach 1% of the original signal intensity. After an hour in the scanner, a loss of about 15% in Cy5 signal intensity may be observed While higher levels of ozone result in damage more quickly, it has been demonstrated that arrays are sensitive to levels of roughly 10 ppb or more during a typical scanning time of a microarray.

Several approaches have been used in effort to address the problem of array degradation by ozone. One regimen contemplates simply storing an array in a container (or cabinet) that is free from ozone. One may simply employ an array/slide holder that is effectively (though not necessarily hermetically) sealed.

Another approach is to limit the effect of ozone by processing an array quickly and scanning it soon thereafter. In a similar approach, another manner of avoiding ozone degradation has been to limit the time for which microarrays remain in a scanner microarray feeder queue. Yet, as alluded to above this goal may sometimes be unattainable in that an entire automated run of, for example, 48 slides (microarrays) can take 8-plus hours.

What is more, an issue of variation in scanning time is present—partly due to scheduling issues, different scan types used by an operator, speeds at which the arrays may be scanned etc.—that adds an undesirable level of uncertainty to scan results. Still further, the point at which a particular array/slide is scanned during a run introduces variability in the degree of signal measured in accordance to array position within the scanning queue (i.e., timing variability is introduced by way of which arrays are scanned sooner, and which arrays are scanned later in the sequence). As long as ozone attack persists, time represents a statistically significant variable Another treatment of the symptoms of array/dye degradation over time has been to provide an array with a protective chemical coating to reduce degradation rates. One such chemical coating is known as the DyeSaver compound sold by Genisphere. Yet, even this approach has potential drawbacks. Specifically, it offers no protection during array drying and is not effective with certain types of oligonucleotide arrays.

On the other hand, array degradation can be prevented if the slides are stored in Nitrogen (or another neutral atmosphere). Though providing an inert atmosphere is not an option, on a larger scale it has also been appreciated that an entire working environment can be scrubbed of harmful gasses. This goal has been accomplished by employing a clean-room type filter system for ozone in the scanner and/or array processing environment—as has been previously done in microchip fabrications facilities. However, the hardware investment, requirement for HVAC installation, and/or energy expenditures can be significant, setup for such a system can be time-consuming and inconvenient to implement, and even then, it will not be 100% effective. Related approaches that have been tried or suggested are to carry out array processing and/or scanning under an ozone-filtered hood or customized "bio-bubble". Even so, these other approaches can involve significant cost or inconvenience.

Instead, the present invention offers a variety of alternative solutions that will be preferred for their avoidance of undue trouble and cost—as in filtering an entire room/building of ozone. Stated otherwise, systems according to the present invention may offer benefits or gains in terms of convenience, and efficiency in protecting arrays from unwanted chemical interaction. As important (or more so), gains may be observed in terms of scanning efficacy by virtue of features of the present invention.

SUMMARY OF THE INVENTION

Whether used in combination with one or more of the above-referenced techniques or alone, the present invention offers a number of superb options in dealing with ozone contamination in the context of array reading or scanning. When the present invention is used in isolation, it offers a solution in a system without any of the above-referenced drawbacks. But when used in combination with the other approaches, the additional benefits the other solutions offer may be worth-while.

In any case, each aspect of the subject invention provides a reader or scanner-specific solution to ozone or other chemical deleterious effects. A first aspect of the invention is to fit a biopolymer array scanner with an ozone filter. This filter will be provided in series with a dust/particulate filter or be used alone Another advantageous aspect of the invention involves pushing intake air through the filter(s) into the body of the reader/scanner, as opposed to drawing air through the reader/scanner and immediately exhausting it.

By pushing air into the reader or scanner, the net positive pressure inside the device ensures that ozone-laden ambient air will not be drawn into and contaminate the system. Yet, when the system is configured to draw or pull air into itself, it may be desired to augment the device with seals not otherwise present in connection with the lid/top of the scanner and/or to more carefully design part interfit tolerances to provide an "air tight" or "near air tight" system.

By any such means, the present invention solves the problem of ozone degradation based array loses in signal intensity while sitting in the scanner. It is applicable to other chemicals/gasses that might degrade array or dye quality resulting in signal loss due to time spent in a scanner or other type of reader.

The present invention also offers potential advantages is providing for more reproducibility to re-scan or re-read the same array multiple times. The invention can also reduce experimental variability due to variation in times that different arrays spend in a scanner carousel (or other multiple-array holder) prior to being scanned, for example to different scan slide positions in a slide queue, or simply different scan types used by the operator, or just variations due to a non-repeatable schedule. Accordingly, a reader employing the teachings of the present invention can produce useful read or scan results in situations where at least some of the plurality of arrays loaded into the device are of the same layout, but may have been exposed to different samples. Even if separated by a large number of slides (resulting in an otherwise-signification delay in reading the slides when ozone or other atmospheric contaminant degradation would) in the reader queue, the results will have significantly decreased variability in obtained signals as a result of variation in exposure time to ozone or other atmospheric contaminants.

The present invention contemplates such hardware to implement the features above as well as scanning methodology as specifically referenced as well as other approaches accomplished with the hardware. In addition, the invention comprises array scan results produced with the subject hardware and/or methodology.

BRIEF DESCRIPTION OF THE DRAWINGS

Each of the figures diagrammatically illustrates aspects of the invention. To facilitate understanding, the same reference numerals have been used (where practical) to designate similar elements that are common to the figures.

DEFINITIONS

Figure 1:
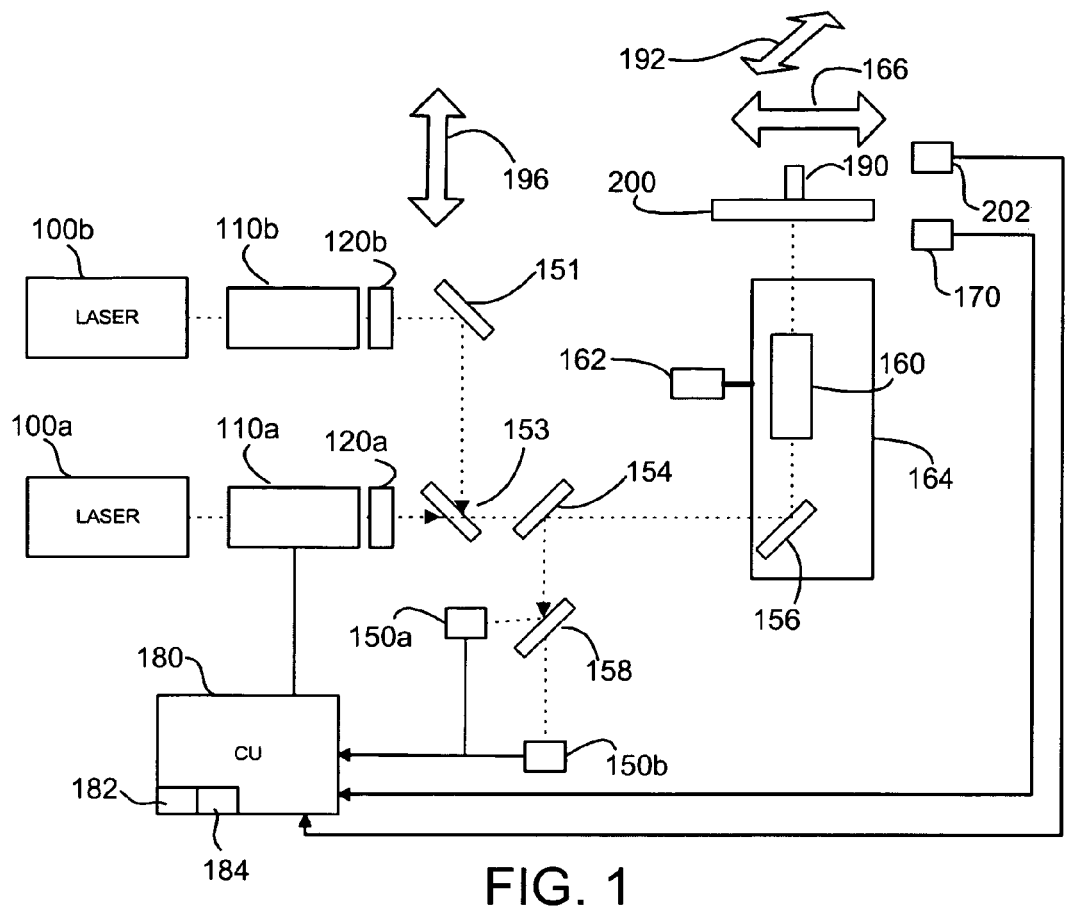
FIG. 1 shows the fundamental components of an optical array scanner system.

Unless defined otherwise, all technical and scientific terms used herein have the same meaning as commonly understood by one of ordinary skill in the art to which this invention belongs. Still, certain elements are defined below for the sake of clarity and ease of reference.

A "biopolymer" is a polymer of one or more types of repeating units. Biopolymers are typically found in biological systems and particularly include polysaccharides (such as carbohydrates), peptides (which term is used to include polypeptides and proteins) and polynucleotides as well as their analogs such as those compounds composed of or containing amino acid analogs or non-amino acid groups, or nucleotide analogs or non-nucleotide groups. Biopolymers include polynucleotides in which the conventional backbone has been replaced with a non-naturally occurring or synthetic backbone, and nucleic acids (or synthetic or naturally occurring analogs) in which one or more of the conventional bases has been replaced with a group (natural or synthetic) capable of participating in Watson-Crick type hydrogen bonding interactions. Polynucleotides include single or multiple stranded configurations, where one or more of the strands may or may not be completely aligned with another. A "nucleotide" refers to a sub-unit of a nucleic acid and has a phosphate group, a 5 carbon sugar and a nitrogen containing base, as well as functional analogs (whether synthetic or naturally occurring) of such sub-units which in the polymer form (as a polynucleotide) can hybridize with naturally occurring polynucleotides in a sequence specific manner analogous to that of two naturally occurring polynucleotides. Biopolymers include DNA (including cDNA), RNA, oligonucleotides, and PNA and other polynucleotides as described in U.S. Pat. No. 5,948,902 and references cited therein (the disclosure of which is incorporated herein by reference), regardless of the source. An "oligonucleotide" generally refers to a nucleotide multimer/polymer) of about 10 to 100 nucleotides in length, while a "polynucleotide" includes a nucleotide multimer having any number of nucleotides. A "biomonomer" references a single unit, which can be linked with the same or other biomonomers to form a biopolymer (e.g., a single amino acid or nucleotide with two linking groups one or both of which may have removable protecting groups).

An "array," includes any one dimensional, two-dimensional or substantially two-dimensional (as well as a three-dimensional) arrangement of addressable regions bearing a particular chemical moiety or moieties (e.g., biopolymers such as polynucleotide sequences (nucleic acids), polypeptides (e.g., proteins), etc.) associated with that region. In the broadest sense, the preferred arrays are arrays of polymeric binding agents, where the polymeric binding agents may be any of: polypeptides, proteins, nucleic acids, polysaccharides, synthetic mimetics of such biopolymeric binding agents, etc. In many embodiments of interest, the arrays are arrays of nucleic acids, including oligonucleotides, polynucleotides, cDNAs, mRNAs, synthetic mimetics thereof, and the like. Where the arrays are arrays of nucleic acids, the nucleic acids may be covalently attached to the arrays at any point along the nucleic acid chain, but are generally attached at one of their termini (e.g. the 3' or 5' terminus). Sometimes, the arrays are arrays of polypeptides, e.g., proteins or fragments thereof.

The term "substrate" as used herein refers to a surface upon which marker molecules or probes, e.g., an array, may be adhered. Glass slides are the most common substrate for biochips, although fused silica, silicon, plastic and other materials are also suitable. The term "flexible" is used herein to refer to a structure, e.g., a bottom surface or a cover, that is capable of being bent, folded or similarly manipulated without breakage. For example, a cover is flexible if it is capable of being peeled away from the bottom surface without breakage. "Flexible" with reference to a substrate or substrate web, references that the substrate can be bent 180 degrees around a roller of less than 1.25 cm in radius. The substrate can be so bent and straightened repeatedly in either direction at least 100 times without failure (for example, cracking) or plastic deformation. This bending must be within the elastic limits of the material. The foregoing test for flexibility is performed at a temperature of 20° C. A "web" references a long continuous piece of substrate material having a length greater than a width. For example, the web length to width ratio may be at least 5/1, 10/1, 50/1, 100/1, 200/1, or 500/1, or even at least 1000/1. The substrate may be flexible (such as a flexible web). When the substrate is flexible, it may be of various lengths including at least 1 m, at least 2 m, or at least 5 m (or even at least 10 m). The term "rigid" is used herein to refer to a structure e.g., a bottom surface or a cover that does not readily bend without breakage, i.e., the structure is not flexible.

Any given substrate may carry one, two, four or more arrays disposed on a front surface of the substrate. Depending upon the use, any or all of the arrays may be the same or different from one another and each may contain multiple spots or features. A typical array may contain more than ten, more than one hundred, more than one thousand, more ten thousand features, or even more than one hundred thousand features, in an area of less than 20 cm$^2$ or even less than 10 cm$^2$. For example, features may have widths (that is, diameter, for a round spot) in the range from a 10 μm to 1.0 cm. In other embodiments each feature may have a width in the range of 1.0 μm to 1.0 mm, usually 5.0 μm to 500 μm, and more usually 10 μm to 200 μm. Non-round features may have area ranges equivalent to that of circular features with the foregoing width (diameter) ranges. At least some, or all, of the features are of different compositions (for example, when any repeats of each feature composition are excluded the remaining features may account for at least 5%, 10%, or 20% of the total number of features). Interfeature areas will typically (but not essentially) be present which do not carry any polynucleotide (or other biopolymer or chemical moiety of a type of which the features are composed). Such interfeature areas typically will be present where the arrays are formed by processes involving drop deposition of reagents. It will be appreciated though, that the interfeature areas, when present, could be of various sizes and configurations.

Each array may cover an area of less than 100 cm$^2$, or even less than 50 cm$^2$, 10 cm$^2$ or 1 cm$^2$. In many embodiments, the substrate carrying the one or more arrays will be shaped generally as a rectangular solid (although other shapes are possible), having a length of more than 4 mm and less than 1 m, usually more than 4 mm and less than 600 mm, more usually less than 400 mm; a width of more than 4 mm and less than 1 m, usually less than 500 mm and more usually less than 400 mm; and a thickness of more than 0.01 mm and less than 5.0 mm, usually more than 0.1 mm and less than 2 mm and more usually more than 0.2 and less than 1.5 mm. With arrays that are read by detecting fluorescence, the substrate may be of a material that emits low fluorescence upon illumination with the excitation light. Additionally in this situation, the substrate may be relatively transparent to reduce the absorption of the incident illuminating laser light and subsequent heating if the focused laser beam travels too slowly over a region. For example, substrate 10 of array package 30 may transmit at least 20%, or 50% (or even at least 70%, 90%, or 95%), of the illuminating light incident on the front as may be measured across the entire integrated spectrum of such illuminating light or alternatively at 532 nm or 633 nm.

An array is "addressable" when it has multiple regions of different moieties (e.g., different polynucleotide sequences) such that a region (i.e., a "feature" or "spot" of the array) at a particular predetermined location (i.e., an "address") on the array will detect a particular target or class of targets (although a feature may incidentally detect non-targets of that feature). Array features are typically, but need not be, separated by intervening spaces. In the case of an array, the "target" will be referenced as a moiety in a mobile phase (typically fluid), to be detected by probes ("target probes") which are bound to the substrate at the various regions. However, either of the "target" or "target probe" may be the one which is to be evaluated by the other (thus, either one could be an unknown mixture of polynucleotides to be evaluated by binding with the other).

A "pulse jet" is a device that can dispense drops/droplets in the formation/fabrication of an array. Pulse jets operate by delivering a pulse of pressure (such as by a piezoelectric or thermoelectric element) to liquid adjacent an outlet or orifice such that a drop will be dispensed therefrom. When the arrangement, selection, and movement of "dispensers" is referenced herein, it will be understood that this refers to the point from which drops are dispensed from the dispensers (such as the outlet orifices or nozzles of pulse jets).

A "drop" in reference to the dispensed liquid does not imply any particular shape, for example a "drop" dispensed by a pulse jet only refers to the volume dispensed on a single activation. A drop that has contacted a substrate is often referred to as a "deposited drop" or "sessile drop" or the like, although sometimes it will be simply referenced as a drop when it is understood that it was previously deposited. The terms "fluid" and "liquid" are used synonymously herein in reference to a solution or other flowable and/or printable medium. Detecting a drop "at" a location includes the drop being detected while it is traveling between a dispenser and that location, or after it has contacted that location (and hence may no longer retain its original shape).

An "array layout" refers to one or more characteristics of the features, such as feature positioning on the substrate, one or more feature dimensions, and an indication of a moiety at a given location. "Hybridizing" and "binding", with respect to polynucleotides, are used interchangeably.

A "scan region" refers to a contiguous (e.g., rectangular) area in which the array spots or features of interest, as defined above, are found. The scan region is that portion of the total area illuminated from which the resulting fluorescence, chemiluminescence, or other optical detection techniques is detected and recorded. For the purposes of this invention, the scan region includes the entire area of the slide scanned in each pass of the lens, between the first feature of interest, and the last feature of interest, even if there exist intervening areas that lack features of interest. The scan region does not, however, include "border regions" or "borders" of the array substrate/slide adjacent slide edges and adjacent to but not including or covered by array features. Generally, any borders around the scan region are less than about 5-15 mm and can be as little as 1 mm or even smaller, for example, if the mechanical design of the slide holder or scanner itself permits it. It is often desirable to lay down features as close to the edge of the substrate as possible so as to maximize the number of probes that may be deposited on a given surface area. As such, in many array configurations, the width of a border, if present, between the scanned arrays and the slide edge does not exceed about 20 mm, usually does not exceed about 10 mm and more usually does not exceed about 5 mm. "Lens position" refers to the relative distance between the lens or optical objective(s) of a scanner and a caddy carrying a slide and/or the slide or array itself.

By "remote location," it is meant a location other than the location at which the array is present and hybridization occurs. For example, a remote location could be another location (e.g., office, lab, etc.) in the same city, another location in a different city, another location in a different state, another location in a different country, etc. As such, when one item is indicated as being "remote" from another, what is meant is that the two items are at least in different rooms or different buildings, and may be at least one mile, ten miles, or at least one hundred miles apart. "Communicating" information references transmitting the data representing that information as electrical signals over a suitable communication channel (e.g., a private or public network). "Forwarding" an item refers to any means of getting that item from one location to the next, whether by physically transporting that item or otherwise (where that is possible) and includes, at least in the case of data, physically transporting a medium carrying the data or communicating the data. An array "package" may be the array plus only a substrate on which the array is deposited, although the package may include other features (such as a housing with a chamber). A "chamber" references an enclosed volume (although a chamber may be accessible through one or more ports). It will also be appreciated that throughout the present application, that words such as "top," "upper," and "lower" are used in a relative sense only.

A "computer-based system" refers to the hardware means, software means, and data storage means used to analyze the information of the present invention. The minimum hardware of the computer-based systems of the present invention comprises a central processing unit (CPU), input means, output means, and data storage means. A skilled artisan can readily appreciate that any one of the currently available computer-based systems is suitable for use in the present invention. The data storage means may comprise a recording of the present information as described above, and a memory access means that can access such a recording.

To "record" data, programming or other information on a computer readable medium refers to a process for storing information, using any such methods as known in the art. Any convenient data storage structure may be chosen, based on the means used to access the stored information. A variety of data processor programs and formats can be used for storage, e.g. word processing text file, database format, etc.

A "processor" references any hardware and/or software combination that will perform the functions required of it. For example, any processor herein may be a programmable digital microprocessor such as available in the form of an electronic controller, mainframe, server or personal computer (desktop or portable). Where the processor is programmable, suitable programming can be communicated from a remote location to the processor, or previously saved in a computer program product (such as a portable or fixed computer readable storage medium, whether magnetic, optical or solid state device based). For example, a magnetic medium or optical disk may carry the programming, and can be read by a suitable reader communicating with each processor at its corresponding station.

Furthermore, the words such as "top", "upper", and "lower" are used in a relative sense only. Also, when one thing is "moved", "moving", "re-positioned", "scanned", or the like, with respect to another, this implies relative motion only such that either thing or both might actually be moved in relation to the other. For example, when dispensers are "moved" relative to a substrate, either the dispensers or substrate may actually be put into motion by the transport system while the other is held still, or both may be put into motion.

DETAILED DESCRIPTION OF THE INVENTION

In describing the invention in greater detail than provided in the Summary and as informed by the Background and Definitions provided above, the pertinent functional aspects of the invention are first described. Next, exemplary components for actually scanning an array are described. This discussion is followed by a brief discussion of methods of using an array as will be protected during scanning by features of the invention. Then, a particular hardware implementation of the present invention is set forth. Finally, kits for use with arrays to be used in connection with scanners according to aspects of the present invention are presented.

Before describing these matters in such detail, however, it is to be understood that this invention is not limited to particular variations set forth and may, of course, vary. Various changes may be made to the invention described and equivalents may be substituted without departing from the true spirit and scope of the invention. In addition, many modifications may be made to adapt a particular situation, material, composition of matter, process, process act(s) or step(s), to the objective(s), spirit or scope of the present invention. All such modifications are intended to be within the scope of the claims made herein.

Methods recited herein may be carried out in any order of the recited events that s logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element (as indicated by use of any permissive term such as the words "may," "might," "possible," etc.). Accordingly, this statement is intended to serve as antecedent basis for use of such exclusive terminology as "solely," "only" and the like in connection with the recitation of claim elements, or use of a "negative" limitation therewith.

Functional Parameters

As summarized above, the invention involves a filter on or within a reader or scanner that reduces or even eliminates the amount of chemicals in the air inside the device that are harmful to the array, or the dye on the array. A known scanner such as the AGILENT MICROARRAY SCANNER manufactured by Agilent Technologies, Palo Alto, Calif. may be employed, or some other instrument used for reading fluorescent dyes (i.e. a microarray imager that uses an imaging rather than scanning lens) that can be harmed with ozone. These fluorescent dyes may be on DNA microarrays but could be in other assays (that would use a microplate reader). Whatever the case, the term "reader" may be used generically in reference to any such devices.

In the case of a scanner such as the Agilent Technologies, Inc. scanner shown in FIG. 3 and discussed further below, the goal of reducing array-attacking chemicals may be accomplished by placing an air filter at the primary air inlet port in order to prevent the harmful contaminants from entering the interior of the device. These contaminants could include ozone, but could also be any chemicals harmful to the array or its dye or RNA probes or targets.

Where the chemical of interest is ozone (though ozone is merely an example of chemical to filter), the filter might be an ozone-scavenging filter such as an activated charcoal filter, or a filter loaded with an ozone-removing catalyst such as manganese dioxide. Such a filter will remove, for example, at least 95% to 99% to 99.9% (expressed in parts per million (ppm)) of the ozone form air run thought the filter. The intent is to provide an ozone concentration in contact with the array of less than about 5, or more preferably less than about 3 to 4 parts per billion (ppb). Testing by applicant has shown that maintaining ozone at these levels is important to avoid quantifiable damage to the array by Ozone. Even so, the invention will offer some relative advantages with less efficient filtering or incomplete filtering (i.e, only 80% to 99% or 95 to 99.9% of the volume of air exposed to the array is run through the filter.) Naturally, the ozone gas and concentrations thereof are exemplary.

Whatever the case, the filter could be provided as a replacement filter to the particulate filter presently provided in the system or in addition to the filter presently used in order to reduce dust content of particulates in air pulled into the scanner to cool its components.

In the current Agilent scanner configuration, a cooling fan blows air out of an exhaust port. This in turn pulls air into the scanner through the inlet port. This approach may be adapted for the present invention.

Yet, in any instrument there can be "leaks" to airflow other than those intended as air channels. Since these leaks will introduce air not filtered of ozone, it may sometimes be preferred to use a circulation fan to blow air into the instrument (forcing it through the filters and into the machine). In this case, the air inflow can be directly filtered and the instrument interior be under positive pressure helping to prevent "leaks".

Otherwise, it may be desired to take steps in order to seal-off potential leaks. Means to do so may include tighter tolerances in between parts, adding supplemental seals, welding (e.g., chemically or ultrasonically) abutting or overtaping seams between constituent parts, and/or designing the scanner without seams by integrating otherwise separate panel pieces.

In either case, the system is preferably adapted such that in passing the airflow through said filter, the array within said reader is only substantially exposed to air passed through said filter. In this context, it is preferred that at least about 90% to 95% volume of incoming air capable of exposure to the array(s) will be passed through the filter. Of course, exactly what defines acceptable leakage or leaking in the context above will have some relation to the efficiency of the filter employed and net resultant concentration of unwanted chemicals in the scanner air.

Scanning Components

The filtration aspects of the invention may be used in conjunction with any of a number of known scanners such as the AGILENT MICROARRAY SCANNER noted above or other suitable apparatus as described in U.S. Pat. Nos. 5,585,639; 5,760,951; 5,763,870; 6,084,991; 6,222,664; 6,284,465; 6,329,196; 6,371,370 and 6,406,849—the disclosures of which are herein incorporated by reference. Furthermore, other scanning devices to which the invention may be applied are commercially available from Axon Instruments in Union City, Calif. and Perkin Elmer of Wellesly, Mass. and still others. Still, the workings of an exemplary optical scanner as may be used in the present invention is shown in FIG. 1.

FIG. 1 shows a two-channel optical scanner, in which the components for each channel are given 'a' and 'b' suffixes. In this system, a light system provides sample excitation light from a source such as a laser 100. The light passes through an electro-optic modulator (EOM) 110 with attached polarizer 120. The lasers 100a and 100b may be of different wavelength (e.g., one providing red light and the other green) and each has its own corresponding EOM 110a, 110b and polarizer 120a, 120b. The beams may be combined along a path toward a holder or caddy 200 by the use of full mirror 151 and dichroic mirror 153. A control signal in the form of a variable voltage applied to each corresponding EOM 110a, 110b by the controller (CU) 180, changes the polarization of the exiting light which is thus more or less attenuated by the corresponding polarizer 120a, 120b. Controller 180 may be or include a suitably programmed processor. Thus, each EOM 110 and corresponding polarizer 120 together act as a variable optical attenuator which can alter the power of an interrogating light beam exiting from the attenuator.

The light from both lasers 100a, 100b is transmitted through a dichroic beam splitter 154, reflected off fully reflecting mirror 156 and focused onto either an array (not shown) mounted on holder 200, or a calibration member (not shown), whichever is at a reading position, using optical components in beam focuser 160. Light emitted (in particular, fluorescence) at two different wavelengths (e.g., green and red light) from features 16, in response to the interrogating light, is imaged using the same optics in focuser/scanner 160, and is reflected off mirrors 156 and 154. The distinct excitation sources are aligned such that the emitted fluorescence interact with a further dichroic mirror 158 and are passed to respective detectors 150a and 150b. More optical components (not shown) may be used between the dichroic and each detector 150a, 150b, splitter 154 or mirror 158 (such as lenses, pinholes, filters, fibers, etc.) and each detector 150a, 150b may be of various different types (e.g., a photo-multiplier tube (PMT) or a CCD or an avalanche photodiode (APD)). All of the optical components, through which light emitted from an array or calibration member in response to the illuminating laser light passes to detectors 150a, 150b, together with those detectors, form a detection system. A scan system causes the illuminating region in the form of a light spot from each laser 100a, 100b, and a detecting region of each detector 150a, 150b (which detecting region will form a pixel in the detected image), to be scanned across multiple regions of an array or an array package mounted on holder 200.

However the detector(s) 150 are configured, the scanned regions for an array will include at least its multiple probe features. The scanning system is typically a line by line scanner, scanning the interrogating light in a line across an array as described below when at the reading position, in a direction of arrow(s) 166, then moving ("transitioning") the interrogating light in a direction into/out of the paper as depicted by arrow(s) 192 as viewed in FIG. 1 when at a position at an end of a line, and repeating the line scanning and transitioning until the entire array has been scanned.

This scanning feature is accomplished by providing a housing 164 containing mirror 156 and focuser 160, which housing 164 can be moved along a line of pixels (i.e., from left to right or the reverse as viewed in FIG. 1) by a transporter 162. The second direction 192 of scanning (line transitioning) can be provided by second transporter, which may include a motor and belt (not shown) to move caddy 200 along one or more tracks. The second transporter may use a same or different actuator components to accomplish coarse (a larger number of lines) movement and finer movement (a smaller number of lines). Generally, directly adjacent rows are scanned. However, "adjacent" rows may include alternating rows or rows where more than one intervening row is skipped.

Of course, the movements 166 and 192 may be accomplished by actuating holder 200 or housing 164 alone. Still further, the movement roles described for each element above may be swapped.

An autofocus detector 170 is generally provided to sense any offset (variation in position) between different regions of array 12 when in the reading position, and a determined position of the focal plane of the detection system. The autofocus system includes detector 170, controller 180, and a motorized or servo-controlled adjuster 190 to move holder 200 in the direction of arrow 196 to establish lens position correct focus for the system. The detector may directly detect a partial reflection from another beamsplitter (not shown) (e.g., between splitters 153 and 154). In addition, a second position detector 202, also feeding back to the CU, preferably measures the absolute position (i.e., relative to the apparatus) of the servo-controlled adjuster 190). As above with respect to movements 166 and 192, it should be observed that focus servo control movement indicated by arrows(s) 196 (i.e., controlling lens position) may occur in connection with housing 164 or focusing optics 160 instead of the holder.

Further details regarding suitable chemical array autofocus hardware is described in pending U.S. patent application Ser. No. 09/415,184 for "Apparatus And Method For Autofocus" by Dorsel, et al., filed Oct. 7, 1999, as well as European publication EP 1091229 published Apr. 11, 2001 to the same title and inventors—the disclosures of which are herein incorporated by reference. Details as to the manner of focusing such hardware, or other suitable hardware, is the subject of the methodology above and as provided in the Example below.

In any case, array orientation and configuration is of little consequence in this context (though it may be in other situations) since focus can be set to probe features either directly, or looking through a transparent substrate medium if the array is reversed for scanning.

Controller 180 of the apparatus is connected to receive signals from detectors 150a, 150b, these different signals corresponding to different "channels," i.e., signals which result at each of the multiple detected wavelengths from emitted light for each scanned region of an array when at the reading position mounted in holder 200. Controller 180 also receives the signal from autofocus offset detector 170 and absolute servo position detector 202, and provides the control signal to EOM 110, and controls the scan system. Controller 180 may also analyze, store, and/or output data relating to emitted signals received from detectors 150a, 150b in a known manner.

Figure 2:
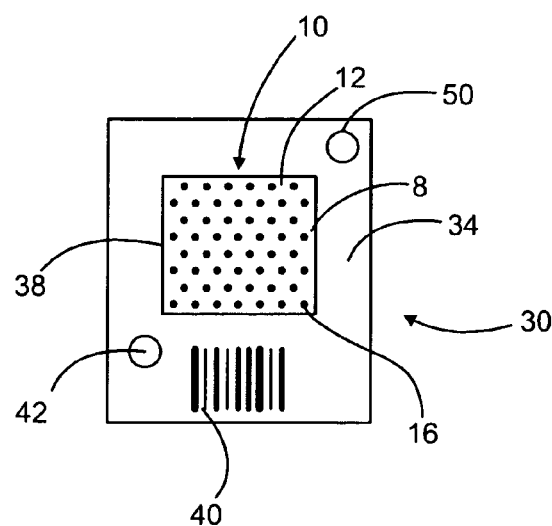
FIG. 2 is a top view of a packaged array that may be used in connection with the present invention.

Controller 180 may include a computer in the form of a programmable digital processor, and include a media reader 182 which can read a portable removable media (such as a magnetic or optical disk), and a communication module 184 which can communicate over a communication channel (such as a network, for example the internet or a telephone network, possibly a wireless network) with a remote site (such as a database at which information relating to array package 30 may be stored in association with the identification 40 as shown in FIG. 2). The scanner of FIG. 1 may further include a reader (not shown) to read an identifier, such as the illustrated bar code from an array package.

Utility

The subject scanners (outfitted with filtration features as required by the present invention) find use in reading arrays utilized in a variety of applications, where such applications are generally analyte detection applications in which the presence of a particular analyte in a given sample is detected at least qualitatively, if not quantitatively. Protocols for carrying out array assays are well known to those of skill in the art and need not be described in great detail here. Generally, the sample suspected of comprising the analyte of interest is contacted with an array under conditions sufficient for the analyte to bind to its respective binding pair member that is present on the array. Thus, if the analyte of interest is present in the sample, it binds to the array at the site of its complementary binding member and a complex is formed on the array surface. The presence of this binding complex on the array surface is then detected, e.g., through use of a signal production system such as an isotopic or radioactive or fluorescent label present on the analyte, etc. The presence of the analyte in the sample is then deduced from the detection of binding complexes on the substrate surface.

Specific analyte detection applications of interest include hybridization assays in which the nucleic acid arrays of the subject invention are employed. In these assays, a sample of target nucleic acids is first prepared, where preparation may include labeling of the target nucleic acids with a label, e.g., a member of signal producing system. Following sample preparation, the sample is contacted with the array under hybridization conditions, whereby complexes are formed between target nucleic acids (or other molecules) that are complementary to probe sequences attached to the array surface. The presence of hybridized complexes is then detected. Specific hybridization assays of interest that may be practiced using the subject arrays include: gene discovery assays, differential gene expression analysis assays; nucleic acid sequencing assays, and the like. References describing methods of using arrays in various applications include U.S.

Pat. Nos. 5,143,854; 5,288,644; 5,324,633; 5,432,049; 5,470,710; 5,492,806; 5,503,980; 5,510,270; 5,525,464; 5,547,839; 5,580,732; 5,661,028; 5,800,992—the disclosures of which are herein incorporated by reference.

Where the arrays are arrays of polypeptide binding agents, e.g., protein arrays, specific applications of interest include analyte detection/proteomics applications, including those described in U.S. Pat. Nos.: 4,591,570; 5,171,695; 5,436,170; 5,486,452; 5,532,128 and 6,197,599 as well as published PCT application Nos. WO 99/39210; WO 00/04832; WO 00/04389; WO 00/04390; WO 00/54046; WO 00/63701; WO 01/14425 and WO 01/40803—the disclosures of which are herein incorporated by reference.

An alluded to above, an exemplary array is presented in FIG. 2. Array 10 carries multiple probe features 16 disposed across a surface of the substrate 12. The substrate is preferably in the form of a contiguous, substantially planar substrate made of transparent material to facilitate data acquisition scanning therethrough. Alternatively, the substrate could be read or scanned from the side that carries features 16. Features 16 (not to scale) are shown disposed in a pattern that defines the array. The extent of the pattern defines a read or scan region 8.

Array 10 may be set within a housing 14 to provide an array package 20. In which case, substrate 12 is sealed (such as by the use of a suitable adhesive) to housing 34 around a margin 38. Housing 34 is configured such that it and substrate 12, define a chamber into which features 16 of the array face. This chamber is accessible through resilient septa 42 and 50 that define normally closed ports of the chamber. An identifier 40, possibly in the form of a bar code, may be affixed to housing 34. The composition of the probe features and material(s) used to produce elements of the array package may vary, but may be as typical in the art.

In use, the array will typically be exposed to a sample (such as a fluorescently labeled analyte, e.g., protein containing sample) and the array will then be read. Reading of the array may be accomplished by illuminating the array and reading the location and intensity of resulting fluorescence at each feature of the array to detect any binding complexes on the surface of the array.

Results from reading an array may be raw results (such as fluorescence intensity readings for each feature in one or more color channels) or may be processed results such as obtained by applying factors to the readings, rejecting a reading for a feature which is above or below a predetermined threshold and/or forming conclusions based on the pattern read from the array (such as whether or not a particular target sequence may have been present in the sample).

The results of the reading (processed or not) may be forwarded (such as by communication) to a remote location if desired, and received there for further use (such as further processing). Stated otherwise, in certain variations, the subject methods may include a step of transmitting data from at least one of the detecting and deriving steps, to a remote location. The data may be transmitted to the remote location for further evaluation and/or use. The same such treatment may be afforded quality control data generated and saved in connection with the diagnostic methodology noted above. In many instances, it may be preferred to pair reading results with quality control information. Any convenient telecommunications means may be employed for transmitting the data, e.g., facsimile, modem, Internet, etc.

Alternatively, or additionally, the data representing array results may be stored on a computer-readable medium of any variety such as noted above or otherwise. Retaining such information may be useful for any of a variety of reasons as will be appreciated by those with skill in the art. The same holds for quality control data (whether it be raw or processed data) produced as described above or otherwise.

Enclosure Components and Filter/Fan Options

Figure 3:
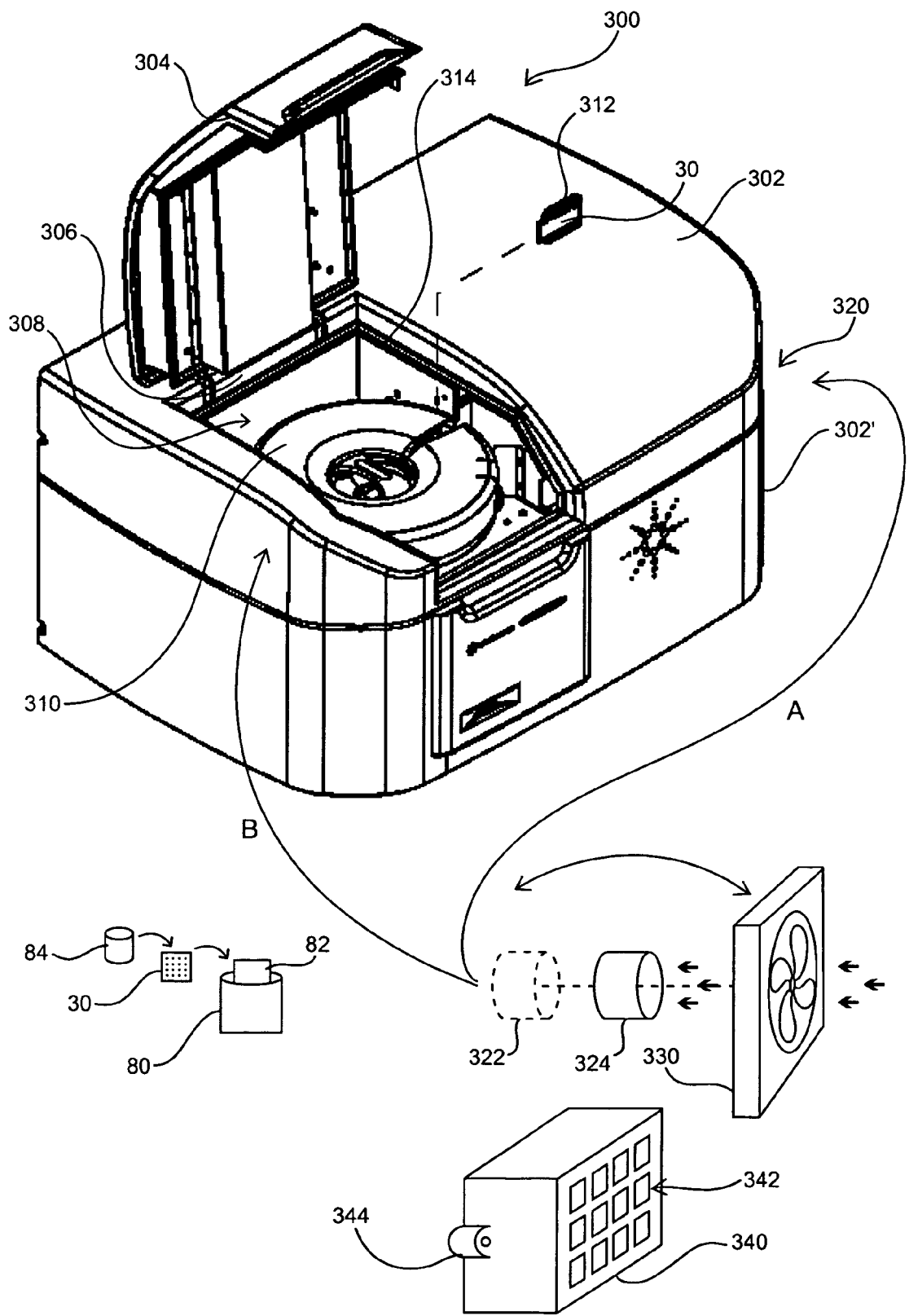
FIG. 3 is a perspective view of a scanner system with components supplied in accordance with aspects of the present invention.

In FIG. 3, the body of an exemplary scanner assembly 300 according to the present invention is shown. At least some of the scanner components described in connection with FIG. 1 are housed within shell or housing portion(s) 302, 302'. A lid or cover 304 pivots about a hinge 306 to enclose the chamber 308 in which the microarray queuing device (in the shape of a carousel 310 (though a linear feed mechanism or another form of holder including multiple receptacles to hold a plurality of microarrays could be used) is set when filled with slides holders 312 carrying arrays 30. Generally, lid 304 will seat against a complementary bead 314.

An air inlet 320 is provided in the right side of the scanner housing as shown in FIG. 3. Of course, it may be provided elsewhere. Its presently located position is provided such that a fan (not shown) in the rear of the unit will draw air across internal electronic componentry and provide a flow of cooling air.

Within scanner assembly 300, a particle filter 322 is typically provided. According to the invention a chemical-scavenging filter 324 will be provided. It may replace the particulate filter when configured for particulate filtering and chemical scavenging. Otherwise, both filters may be employed—either one in front of the other, though it may be desired to filter particulates first. As treated variously herein, the chemical filter 324 is preferably an ozone filter, though others might be usefully employed (e.g., a reactive gas filter, that would remove acidic or alkaline gases, or an organic vapor filter that would remove fluorocarbons, hydrocarbons, and the like) In any case, a suitable ozone filter is provided by NICHIAS Corporation, the Honeycle ZG and Honeycle ZCI models.

Other optional aspects of the implementation of the invention concern the manner in which airflow is provided through the scanner. One option discussed above is to continue to employ a fan that draws air through an inlet to the scanner assembly by creating a partial vacuum within the device by pushing air therefrom. Another option is to provide a fan 330 set in front of or behind the filters to push air into the scanner. Such optional placement is indicated by the double-headed arrow. Whatever the flow arrangement selected, for application in the AGILENT MICROARRAY SCANNER shown, the assembly 322, 324, 330 may simply be set at the units existing air intake 320 (referenced above) as indicated by arrow "A" thereto.

An alternate placement approach involves locating the fan/filter combination 322, 324, 330 such that chamber 308 is directly provided with filtered air. Chamber 308 is, of course, the region of the reader where the arrays are stored in the holder/carousel. By specifically filtering air provided to this area (as indicated by placing the filter(s)/fan (e.g., as indicated by arrow "B") in direct communication with the chamber, any air mixture between this zone and others in the system is deliberately avoided. In accordance with this second, advantageous placement option in which filtering is applied directly at the site of interest, the existing cooling fan in the system may be retained. In instances where filter air is drawn into chamber 308, the chamber is advantageously sealed to avoid any leakage of unfiltered air thereto.

However, in all of the variations of the invention, an approach where air is pushed into at least the array/slide holding portion of the scanner is advantageous—as noted above—in that it naturally accounts for leaks generated between in the scanner housing pieces (302, 302', etc.) and the lid/bead interface or other ports of possible air entry. In essence, the positive pressure within system 300 will cause filtered air to push out of the leaking areas, minimizing the amount of chemical/ozone contaminated air that can enter into or invade the area containing the array slides.

Still, where a negative internal pressure type system is employed, it is to be appreciated that the filtering system still may offer significant improvement over known techniques. Actually, such a system may be desired from the sake of ease of implementation in retrofitting an existing scanner such as the AGILENT MICROARRAY SCANNER referenced above.

Yet, even for a system where air is drawn through the filter(s) into the scanner body or housing, manufacturing tolerances can be maintained and features such as a lid lockdown and seal at bead 314 provided to minimize any "leaks". Such optional features may be provided through the execution of routine design skill as possessed by those in the relevant art.

Kits

As also illustrated in FIG. 3, kits for use in connection with the subject scanner 300 will include at least one of the arrays 30 as described above in a wrapper 80. Especially in the kits including one or more arrays, it may be desired to further include one or more additional components necessary for carrying out an analyte detection assay, such as one or more sample preparation reagents, buffers and the like. As such, the kits may include one or more containers 84 such as vials or bottles, with each container containing a separate component for the assay, and reagents for carrying out an array assay such as a nucleic acid hybridization assay or the like. The kits may also include buffers (such as hybridization buffers), wash mediums, enzyme substrates, reagents for generating a labeled target sample such as a labeled target nucleic acid sample, negative and positive controls. Written instructions (e.g., for using the array assay devices for carrying out an array based assay-may be provided in the kit.

Any instructions are generally recorded on a suitable recording medium. For example, the instructions may be printed on a substrate, such as paper or plastic, etc. As such, the instructions may be present in the kits as a package insert 82, in the labeling of the container of the kit or components thereof (i.e., associated with the packaging or subpackaging), etc. In other embodiments, the instructions are present as an electronic storage data file present on a suitable computer readable storage medium 84, e.g., CD-ROM, diskette, etc., including the same medium on which the program is presented.

In yet other embodiments, the instructions are not themselves present in the kit, but means for obtaining the instructions from a remote source, e.g. via the Internet, are provided. An example of this embodiment is a kit that includes a web address where the instructions can be viewed and/or from which the instructions can be downloaded. Conversely, means may be provided for obtaining the subject programming from a remote source, such as by providing a web address. Still further, the kit may be one in which both the instructions and software are obtained or downloaded from a remote source, as in the Internet or World Wide Web. Of course, some form of access security or identification protocol may be used to limit access to those entitled to use the subject invention. As with the instructions, the means for obtaining the instructions and/or programming is generally recorded on a suitable recording medium.

In another sort of kit, fan 330 and/or filter elements 322, 324 may be provided in a retrofit kit to attach to an unmodified scanner to provide a solution according to an aspect of the present invention. Such a kit may additionally include a housing 340 in packaged combination with any necessary electronics or cabling (such as in the case fan 330 is to be provided in addition to any fan already within the system). Housing may include a grill section 342, bosses 344 to facilitate bolt-on affixation to scanner 330 and internal support interfaces for such elements to be provided therein. Particulars of any such design and directions that may be included in a kit therewith may vary.

It is evident from the above discussion that the above-described invention provides an effective and readily applicable way to offer flexibility in the selection of various methods to control degradation of microarrays due to environmental gases. As such, the subject invention represents a significant contribution to the art of microarray scanning or reading.

All publications and patents cited in this specification are herein incorporated by reference as if each individual publication or patent were specifically and individually indicated to be incorporated by reference (except insofar as any may conflict with the present application—in which case the present application prevails). The citation of any publication is for its disclosure prior to the filing date and should not be construed as an admission that the present invention is not entitled to antedate such publication by virtue of prior invention.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, operation, to the objective, spirit and scope of the present invention. Indeed, the techniques described herein can be applied, especially, in various imaging and scanning or reading applications involving fluorescent labeling or other chemical features susceptible to ozone or other airborne chemicals or compounds prone to degrade reader results. All such modifications are intended to be within the scope of the invention, of which aspects are expressed in the following claims.

What is claimed is:

1. A method of reading an addressable array of two or more ligands, said method comprising:
   providing an optical array reader comprising a chemical-scavenging filter and said addressable array,
   loading said reader with said addressable array,
   providing an airflow within said reader,
   passing said airflow through said filter, wherein said addressable array within said reader is only substantially exposed to air passed through said filter, and
   reading said addressable array to detect any binding complex on said array.

2. The method of claim 1, wherein said reader is loaded with a plurality of addressable arrays, which are read in turn.

3. The method of claim 2, wherein said reader is loaded with plurality of addressable arrays placed within a holder.

4. The method of claim 1, wherein said airflow within said reader is provided under positive pressure.

5. The method of claim 1, wherein said airflow within said reader is provided under negative pressure.

6. The method of claim 1, wherein said chemical scavenging filter at least filters ozone.

7. The method of claim 1, wherein said addressable array is a biopolymer array.

8. The method of claim 7, wherein the biopolymer is selected from the group consisting of polypeptides and nucleic acids.

9. The method of claim 7, further comprising;
providing a kit comprising said biopolymer array; and
retrieving said biopolymer array from said kit.

10. The method of claim 1, wherein said airflow through said filter is provided directly to a chamber holding said addressable array.

11. The method of claim 9, wherein said kit further comprises instructions.

12. The method of claim 2 wherein the plurality of addressable arrays comprise arrays of the same array layout.

13. The method of claim 1, further comprising transmitting results of said reading from a first location to a second location.

14. The method of claim 13, where said second location is a remote location.

15. The method of claim 1, further comprising receiving data representing a result of said reading.

* * * * *